(12) United States Patent
Sakagawa

(10) Patent No.: US 9,295,382 B2
(45) Date of Patent: Mar. 29, 2016

(54) OPHTHALMIC APPARATUS, CONTROL METHOD OF OPHTHALMIC APPARATUS AND STORAGE MEDIUM

(75) Inventor: Yukio Sakagawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 112 days.

(21) Appl. No.: 13/598,791

(22) Filed: Aug. 30, 2012

(65) Prior Publication Data

US 2013/0195337 A1   Aug. 1, 2013

(30) Foreign Application Priority Data

Jan. 26, 2012   (JP) ................................ 2012-014577

(51) Int. Cl.
  *A61B 3/12* (2006.01)
  *A61B 3/10* (2006.01)

(52) U.S. Cl.
  CPC .. *A61B 3/102* (2013.01); *A61B 3/12* (2013.01)

(58) Field of Classification Search
  None
  See application file for complete search history.

(56) References Cited

U.S. PATENT DOCUMENTS

| | | | |
|---|---|---|---|
| 7,641,338 B2 | 1/2010 | Fukuma et al. | |
| 7,677,729 B2 | 3/2010 | Vilser et al. | |
| 7,794,083 B2 | 9/2010 | Tsukada et al. | |
| 8,098,278 B2 | 1/2012 | Yumikake et al. | |
| 2005/0157259 A1 | 7/2005 | Akita et al. | |
| 2007/0070295 A1* | 3/2007 | Tsukada et al. | 351/206 |
| 2007/0222946 A1* | 9/2007 | Fukuma et al. | 351/206 |
| 2007/0244396 A1 | 10/2007 | Vilser et al. | |
| 2008/0151187 A1* | 6/2008 | Tsukada et al. | 351/206 |
| 2010/0118132 A1 | 5/2010 | Yumikake et al. | |
| 2010/0142780 A1 | 6/2010 | Yasuno et al. | |
| 2010/0238403 A1* | 9/2010 | Kobayashi et al. | 351/206 |
| 2011/0234785 A1 | 9/2011 | Wanda et al. | |
| 2012/0044499 A1 | 2/2012 | Shimoyama et al. | |
| 2012/0075640 A1 | 3/2012 | Sakagawa et al. | |

FOREIGN PATENT DOCUMENTS

| | | |
|---|---|---|
| CN | 1947652 A | 4/2007 |
| CN | 101040777 A | 9/2007 |
| CN | 101204318 A | 6/2008 |
| EP | 1882445 A2 | 1/2008 |
| EP | 2172149 A1 | 4/2010 |
| JP | 04-187139 A | 7/1992 |
| JP | 2007-283105 A | 11/2007 |
| JP | 2008-289642 A | 12/2008 |
| JP | 4262603 B2 | 5/2009 |

(Continued)

OTHER PUBLICATIONS

Apr. 24, 2013 Great Britain Official Action in Great Britain Patent Appln. No. GB1300673.9.

(Continued)

*Primary Examiner* — Jon Chang
(74) *Attorney, Agent, or Firm* — Fitzpatrick, Cella, Harper & Scinto

(57) ABSTRACT

An ophthalmic apparatus comprises an imaging unit which images a fundus of an eye to be examined; a calculation unit which calculates a displacement of an imaging position of the imaging unit between fundus images captured by the imaging unit; and a display control unit which causes a display unit to display a fundus image captured by the imaging unit and a region of interest so as to locate the region of interest at a predetermined position on the fundus image based on the displacement calculated by the calculation unit.

20 Claims, 9 Drawing Sheets

(56) References Cited

FOREIGN PATENT DOCUMENTS

| | | |
|---|---|---|
| JP | 2010-110391 A | 5/2010 |
| JP | 2010-227610 A | 10/2010 |
| JP | 2011-115301 A | 6/2011 |
| WO | 03/070090 A2 | 8/2003 |
| WO | 2011/111851 A1 | 9/2011 |
| WO | 2013/018814 A1 | 2/2013 |

OTHER PUBLICATIONS

Jul. 3, 2014 Chinese Official Action in Chinese Patent Appln. No. 201310030481.6.

* cited by examiner

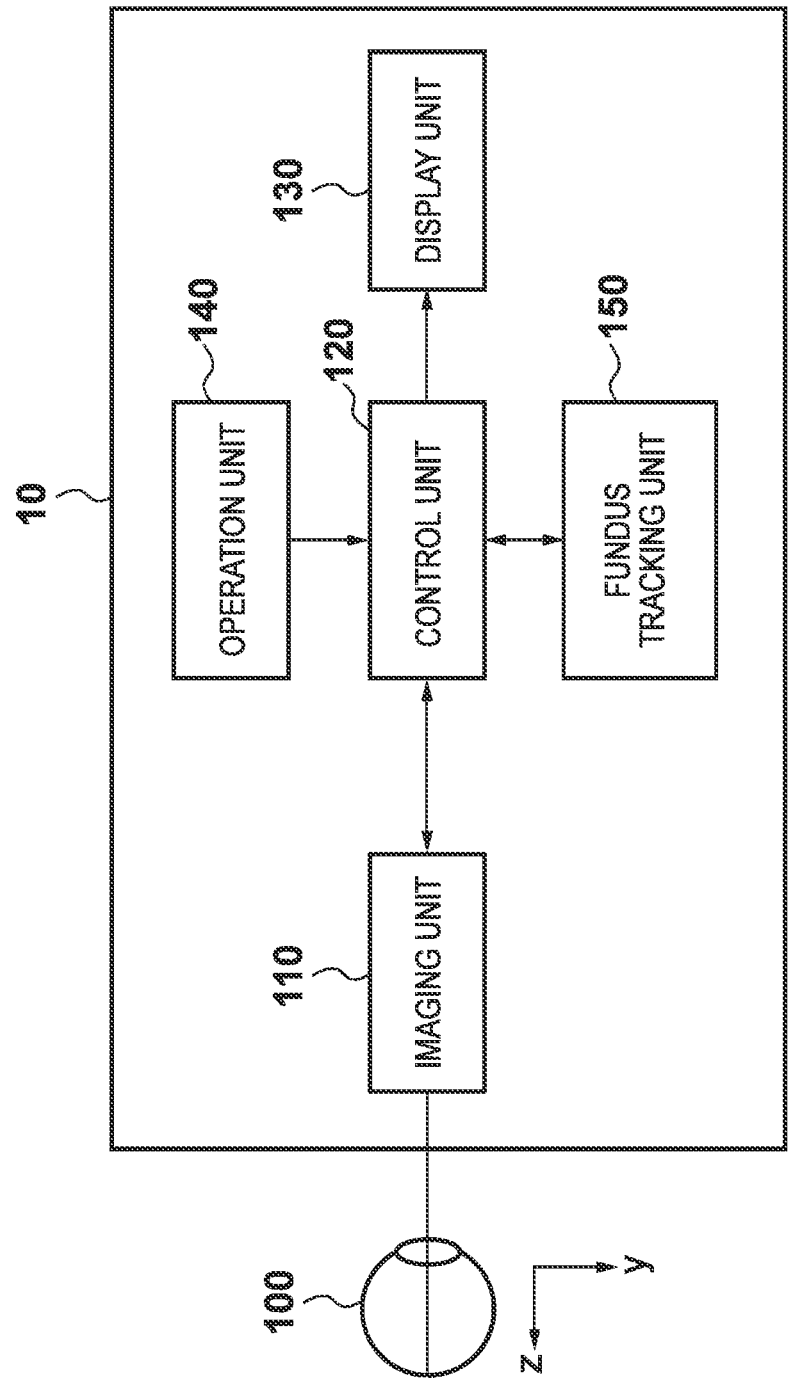

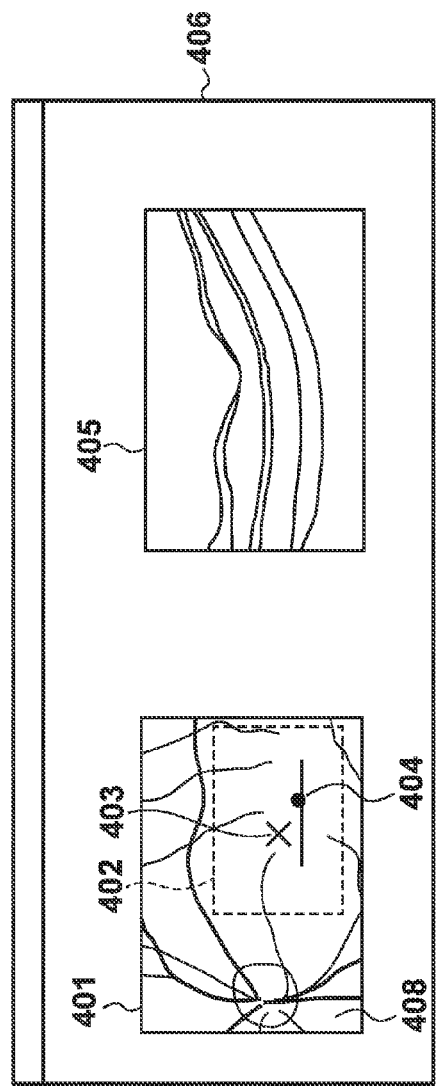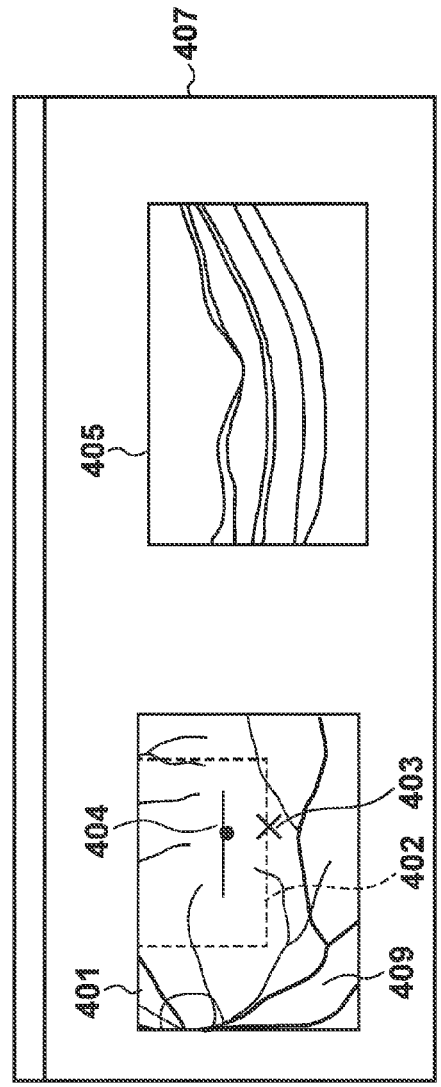
FIG. 4A
FIG. 4B

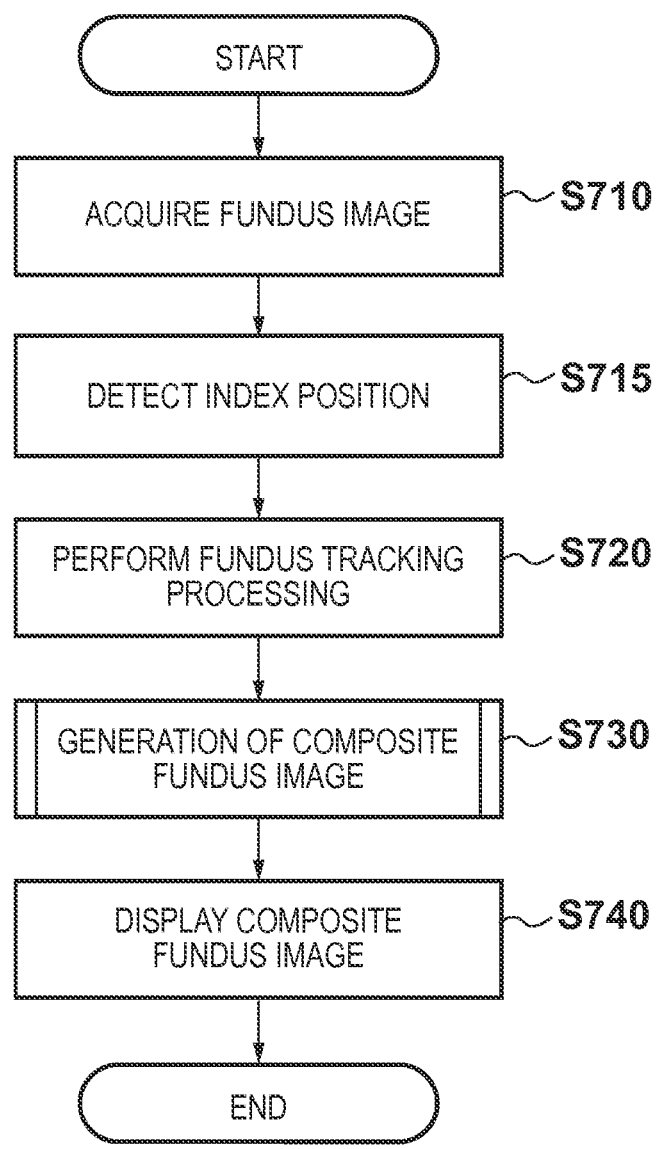

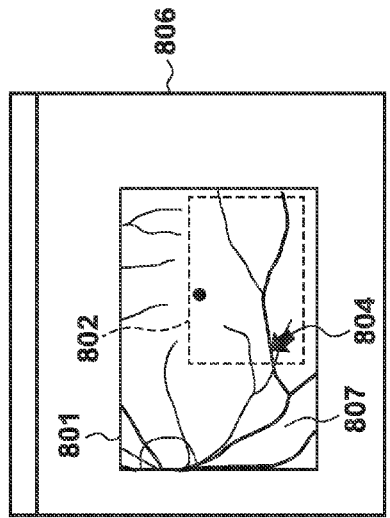
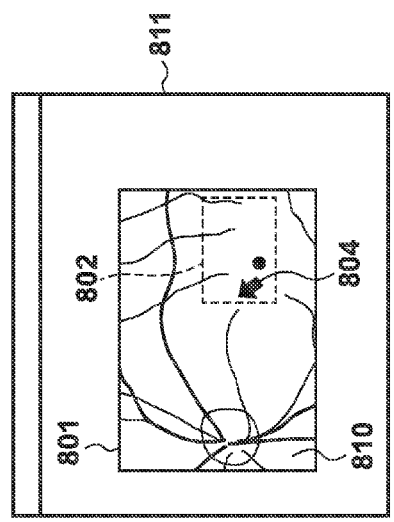
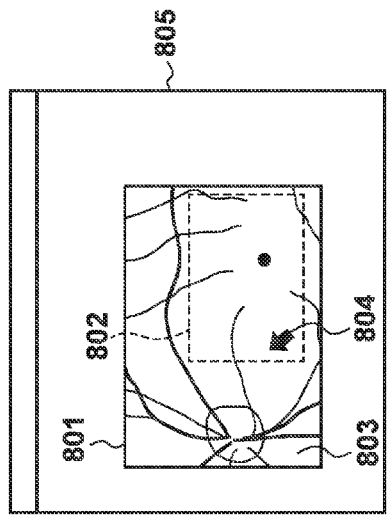
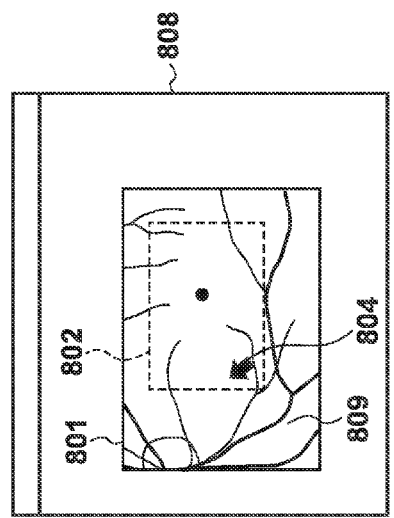

OPHTHALMIC APPARATUS, CONTROL METHOD OF OPHTHALMIC APPARATUS AND STORAGE MEDIUM

BACKGROUND OF THE INVENTION

1. Field of the Invention

The present invention relates to an ophthalmic apparatus, a control method of the ophthalmic apparatus, and a storage medium.

2. Description of the Related Art

An ophthalmic tomographic apparatus such as an OCT (Optical Coherence Tomography) allows three-dimensional observation of the internal state of the retinal layer. This apparatus is effective in diagnosing diseases more accurately, and hence has recently attracted much attention.

Japanese Patent Laid-Open No. 2010-227610 discloses a technique of setting imaging parameters for OCT images based on the measurement position designated on a fundus image of the eye to be examined. Japanese Patent No. 4262603 discloses a technique of correcting an OCT imaging position while tracking the fundus to capture OCT images at the same position on the retina because of the fine fixation movement of the eye to be examined.

According to Japanese Patent Laid-Open No. 2010-227610, however, although this technique sets control parameters for a scanner which operates OCT measurement light based on the position designated on a still fundus image, it gives no consideration to the influence of fine fixation movement. When capturing an OCT image while tracking the fundus as in Japanese Patent No. 4262603, this technique faces the problem that the position of a region of interest designated on a fundus image may differ from the actual imaging position of a tomographic image.

SUMMARY OF THE INVENTION

In consideration of the above problems, it is an object of the present invention to properly display a region of interest on a fundus image.

Note that it is another object of the present invention to obtain functions and effects that can be achieved by the respective arrangements in the mode for carrying out the invention to be described later but cannot be obtained by the prior art.

According to one aspect of the present invention, there is provided an ophthalmic apparatus comprising: an imaging unit which images a fundus of an eye to be examined; a calculation unit which calculates a displacement of an imaging position of the imaging unit between fundus images captured by the imaging unit; and a display control unit which causes a display unit to display a fundus image captured by the imaging unit and a region of interest so as to locate the region of interest at a predetermined position on the fundus image based on the displacement calculated by the calculation unit.

According to one aspect of the present invention, there is provided a control method for an ophthalmic apparatus comprising an imaging unit, a calculation unit, and a display control unit, the method comprising: an imaging step of causing the imaging unit to image a fundus of an eye to be examined; a calculation step of causing a calculation unit to calculate a displacement of an imaging position of the imaging unit between fundus images captured in the imaging step; and a display control step of causing a display control unit to cause a display unit to display a fundus image captured in the imaging step and a region of interest so as to locate the region of interest at a predetermined position on the fundus image based on the displacement calculated in the calculation step.

Further features of the present invention will be apparent from the following description of exemplary embodiments with reference to the attached drawings.

BRIEF DESCRIPTION OF THE DRAWINGS

FIG. 1 is a block diagram showing an example of the arrangement of an ophthalmic apparatus 10 according to the first embodiment;

FIGS. 4A and 4B are views each showing a display example on a display unit 130 of the ophthalmic apparatus 10 according to the first embodiment;

FIG. 7 is a flowchart showing an example of a procedure for processing by an ophthalmic apparatus 10 according to the third embodiment; and FIGS. 8A to 8D are views each showing a display example on a display unit 130 of the ophthalmic apparatus 10 according to the third embodiment.

DESCRIPTION OF THE EMBODIMENTS

Figure 2A:
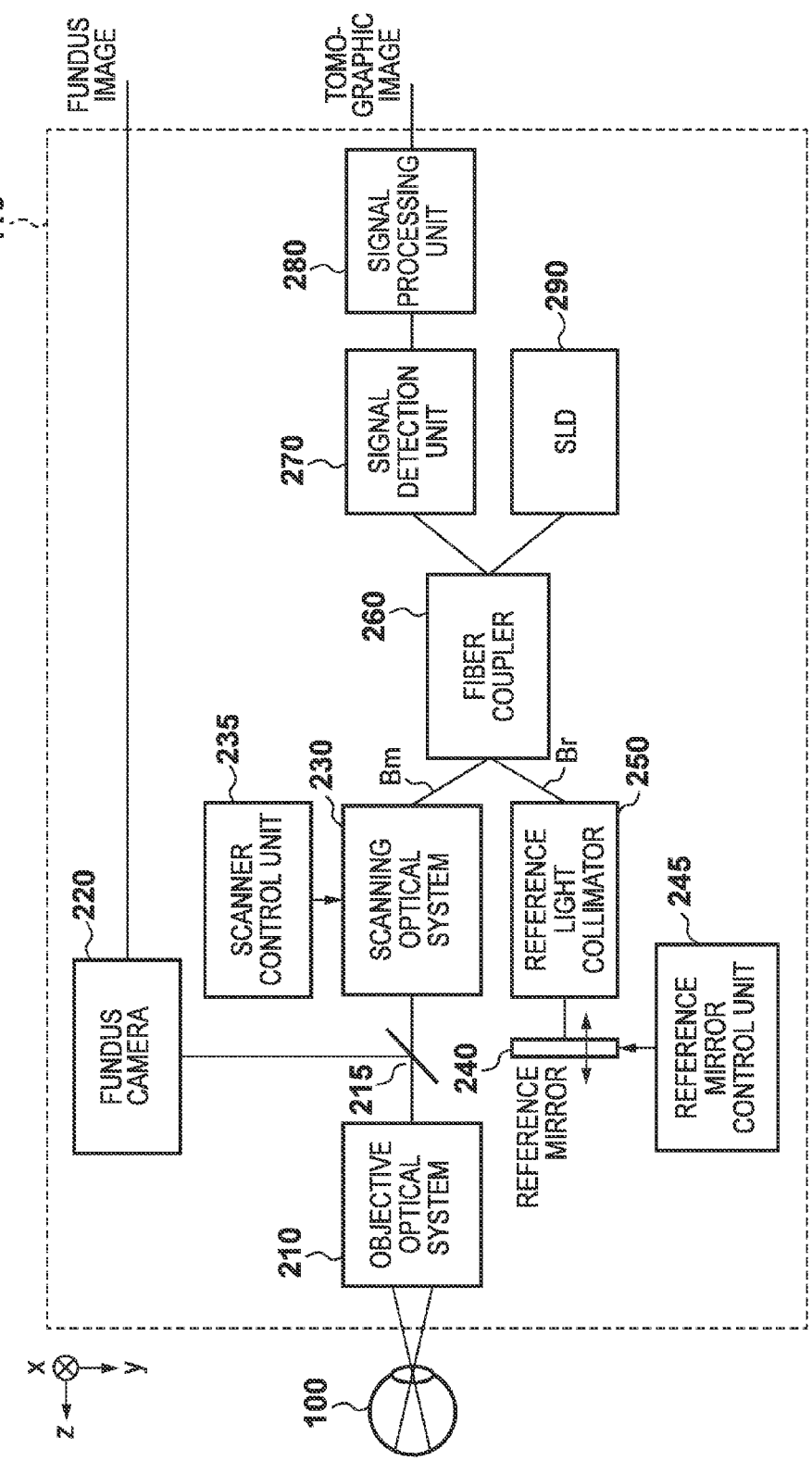
FIGS. 2A to 2C are views showing an example of the arrangement of an imaging unit 110 according to the first embodiment.

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

(First Embodiment)

This embodiment will exemplify a case in which when capturing a tomographic image of the fundus while tracking the fundus, the apparatus displays a fundus image and a region of interest indicating the position of a tomographic image so as to locate the region of interest at a predetermined position on the fundus image.

An example of the arrangement of an ophthalmic apparatus 10 according to the first embodiment will be described first with reference to FIG. 1. The ophthalmic apparatus 10 includes an imaging unit 110, a control unit 120, a display unit 130, an operation unit 140, and a fundus tracking unit 150. The functions of the respective processing units will be sequentially described below.

<Function of Imaging Unit 110>

The imaging unit 110 functions as a fundus imaging unit which captures a two-dimensional image (fundus image) of the fundus of an eye 100 to be examined or a tomographic unit which captures a tomographic image of the eye 100. An example of the arrangement of the imaging unit 110 will be described with reference to FIG. 2A. The imaging unit 110 includes an objective optical system 210, a half mirror 215, a fundus camera 220, a scanning optical system 230, a scanner control unit 235, a reference mirror 240, a reference mirror control unit 245, a reference light collimator 250, a fiber coupler 260, a signal detection unit 270, a signal processing unit 280, and an SLD 290.

The imaging unit 110 uses a spectral domain scheme of generating a tomographic image by performing a Fourier transform of the signal detected by spectroscoping interfering light. Referring to FIG. 2A, the depth direction perpendicular to the drawing surface will be referred to as the X-axis; a measurement light scan in the X-axis direction, a horizontal scan; the downward direction on the drawing surface, the Y-axis; and a scan in the Y-axis direction, a vertical scan.

Referring to FIG. 2A, the light emitted from the SLD 290 which is a low-coherence light source enters the fiber coupler 260. The fiber coupler 260 separates incident light into measurement light Bm and reference light Br. The measurement light Bm is output to the scanning optical system 230 through the optical fiber. The reference light Br is output to the reference light collimator 250 in the same manner.

The scanning optical system 230 scans measurement light by focusing the incident measurement light Bm to a galvano mirror (not shown). The galvano mirror is constituted by a scanner for horizontal scanning and a scanner for vertical scanning. The scanner control unit 235 drives and controls the two scanners. The scanned measurement light Bm reaches the retina of the eye 100 through the objective optical system 210. This light is reflected by the retina, propagates again through the objective optical system 210 and the scanning optical system 230, and reaches the fiber coupler 260. The reference mirror 240 reflects the reference light Br output from the fiber coupler 260 to the reference light collimator 250. The light then reaches again the fiber coupler 260 through the reference light collimator 250.

The measurement light Bm and the reference light Br which have reached the fiber coupler 260 interfere with each other to form interfering light. The interfering light is output from the fiber coupler 260 to the signal detection unit 270. Note that the reference mirror control unit 245 drives and controls the position of the reference mirror 240. It is possible to change the optical path length of reference light by changing the position of the reference mirror 240.

The signal detection unit 270 detects the interfering light output from the fiber coupler 260 and outputs the detected light as an electrical interference signal to the signal processing unit 280. The signal processing unit 280 performs signal processing such as a Fourier transform for the interference signal to generate a signal corresponding to the reflectance along the Z direction of the retina (to be referred to as an "A-scan" signal hereinafter), thereby acquiring a tomographic image of the retina.

The apparatus further captures a fundus image by using the fundus camera 220 and the half mirror 215. Although an infrared camera is used as the fundus camera 220 in this case, the apparatus may use an SLO (confocal scanning laser ophthalmoscope) or the like to capture a fundus image. Note that a fixation target projection unit (not shown) electronically generates a fixation target and projects it onto the retina of the eye 100, thereby stabilizing the fixation. The fixation target projection unit projects a fixation target onto the eye 100 based on various parameters such as the projection position, size, and shape of the fixation target, and a lighting/blinking state.

Figure 2B:
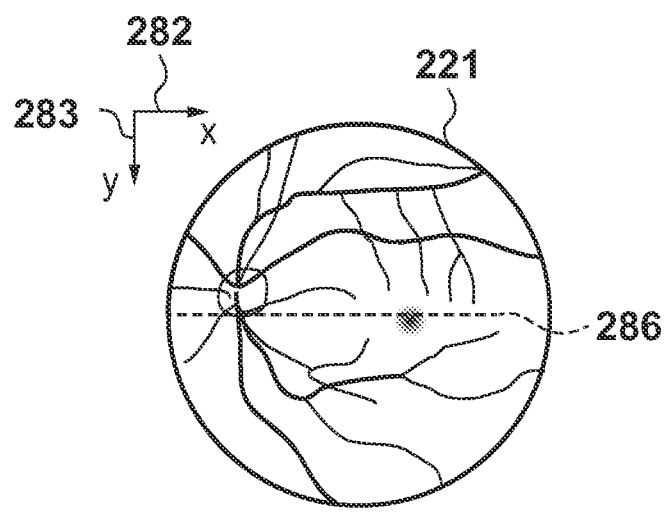
Figure 2C:
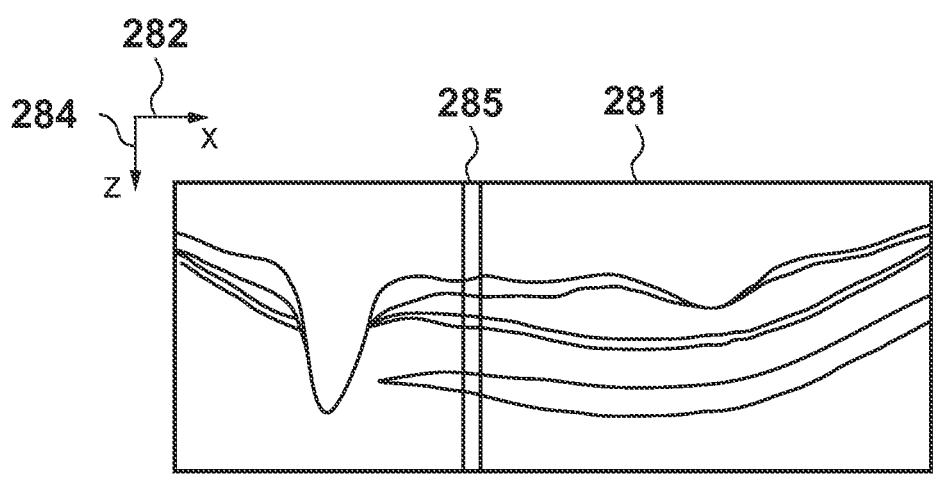

Examples of the fundus image and tomographic image acquired by the imaging unit 110 will be described next with reference to FIGS. 2B and 2C. FIG. 2B shows a fundus image 221. FIG. 2C shows a tomographic image 281 of the retina. Referring to FIGS. 2B and 2C, an arrow 282 represents the direction of a horizontal scan (X direction); an arrow 283, the direction of a vertical scan (Y direction); and an arrow 284, the depth direction of an A-scan (Z direction).

In order to acquire the tomographic image 281, the imaging unit 110 reconstructs each A-scan 285 by using the signal processing unit 280 while moving the galvano mirror of the scanning optical system 230 in the main scanning direction (the horizontal direction in this case) by using the scanner control unit 235, thereby forming one tomographic image 281. The tomographic image 281 is called a B-scan image, which corresponds to a two-dimensional slice in the depth direction relative to the retina and a direction perpendicular to the depth direction, that is, a plane defined by the X-axis and the Y-axis. A dotted line 286 indicates the imaging position of the tomographic image 281. Note that the fundus camera 220 captures the fundus image 221 of the eye 100.

<Function of Control Unit 120>

The control unit 120 generates imaging control information based on the signal output from the operation unit 140, transfers the information to the imaging unit 110, and displays various kinds of images on the display unit 130. A CPU (Central Processing Unit) implements the function of the control unit 120 by executing programs recorded on a memory (not shown). The control unit 120 includes an imaging control unit 120A and a display control unit 120B (neither of which is shown).

The imaging control unit 120A generates imaging control information and outputs it to the imaging unit 110 in accordance with the operation signal input by the operator with the operation unit 140. The imaging control unit 120A acquires a fundus image and tomographic image of the eye 100 from the imaging unit 110. Imaging control information includes information associated with the imaging position, imaging angle, and imaging region of a tomographic image. The imaging position, imaging angle, and imaging region of a tomographic image indicate the position and range of a scan on the retina with measurement light for the acquisition of a tomographic image. These pieces of information are converted into control parameters with which the scanner control unit 235 including the imaging unit 110 controls the scanning optical system 230. In addition, imaging control information may include fixation target control information for controlling the fixation target for guiding the fixation of the eye 100. Note that the imaging control information to be used is not limited to this and may include control information for the reference mirror 240 and focus control information for the objective optical system 210.

The display control unit 120B processes the fundus image and tomographic image acquired by the imaging control unit 120A and makes the display unit 130 display the resultant images. More specifically, the display control unit 120B generates a composite fundus image by superimposing a region of interest on a fundus image of the eye 100 captured by the imaging unit 110 in accordance with the imaging control information generated by the imaging control unit 120A, and displays the image on the display unit 130. The region of interest superimposed on the fundus image indicates, for example, the imaging position of an OCT image and an imaging region on the OCT image. The region of interest is displayed on the fundus image with a line or frame indicating the region of interest. In addition, the lighting position of a fixation lamp on a fundus image may be indicated by a point, circle, or cross.

The display control unit 120B also performs display control on a GUI or the like for input operation by the operator. In addition, the display control unit 120B displays, on the display unit 130, an index which can be moved in accordance with an instruction from the operation unit 140 and can indicate an arbitrary instructed position on the display unit 130. As the index to be used, for example, an arrow-shaped cursor can be used but the invention is not limited to this. An index in any other form can be used as long as it can indicate an arbitrary position on the display unit 130. This makes it possible to issue instruction to change a region of interest.

The display control unit 120B can recognize coordinates on the display unit 130, and can recognize a specific region on the display unit 130 on which the index exists, based on an operation signal input from the operation unit 140. The display control unit 120B can also recognize coordinates on a region on the display unit 130 on which a fundus image is displayed. If, therefore, the operation unit 140 is a mouse, it is possible to recognize the position of the index on the display unit 130 which moves in accordance with the movement of the mouse, based on an operation signal indicating the movement of the mouse. In addition, it is possible to recognize whether the index which moves in accordance with the operation of the operation unit 140 exists on a region on the display unit 130 on which a fundus image is displayed. The display control unit 120B can recognize the specific position at which the index is displayed relative to the coordinates of a fundus image.

<Function of Display Unit 130>

The display unit 130 displays the image processed by the display control unit 120B and a GUI layout. The display unit 130 also displays an index such as an arrow-shaped cursor and other kinds of information.

<Function of Operation Unit 140>

The operation unit 140 outputs an operation signal representing the operation by the operator (not shown) on the control unit 120 in accordance with the operation by the operator. As the operation unit 140, various types of devices such as a mouse, keyboard, and touch panel can be used. Consider a case in which the operation unit 140 is a mouse including a button and a wheel. Upon accepting temporary pressing operation (clicking) on the operation unit 140 (mouse), the operation unit 140 outputs, to the control unit 120, an operation signal indicating that the operation unit 140 has been clicked. When the operator rotates the wheel of the operation unit 140 (mouse), the operation unit 140 outputs, to the control unit 120, an operation signal indicating the rotation amount of the wheel and an operation signal indicating the rotating direction of the wheel. In addition, when the operation unit 140 (mouse) moves, the operation unit 140 outputs an operation signal indicating the movement to the control unit 120. Note that the operation unit 140 may be constituted by one device such as a mouse or a keyboard or two or more devices. For example, the operation unit 140 may be constituted by a mouse and a keyboard.

<Function of Fundus Tracking Unit 150>

The fundus tracking unit 150 analyzes the motion of the retina of the eye 100 from the fundus image captured by the imaging unit 110 to calculate the displacement amount of the fundus. If there are the first and second fundus images captured at two different times, the following processing is performed. The fundus tracking unit 150 sets an ROI 1 (region of interest 1) on the first fundus image and records the position of the ROI 1. Assume that the ROI 1 is a region including an image feature amount such as a strong contrast on the first fundus image. The fundus tracking unit 150 searches for an ROI 2 (region of interest 2) having the highest correlation with the ROI 1 on the second fundus image. The relative difference between the position of the ROI 1 and the position of the ROI 2 is the displacement amount of the fundus.

Figure 5A:
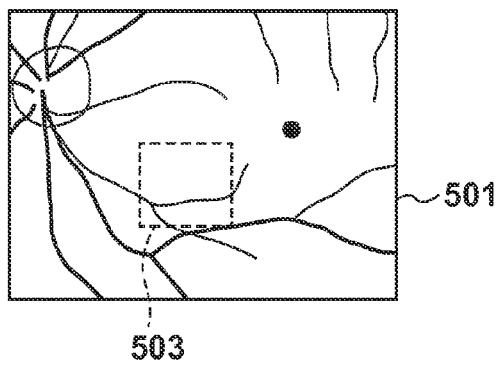
FIGS. 5A and 5B are views each for explaining an example of the operation of a fundus tracking unit 150 according to the first embodiment.
Figure 5B:
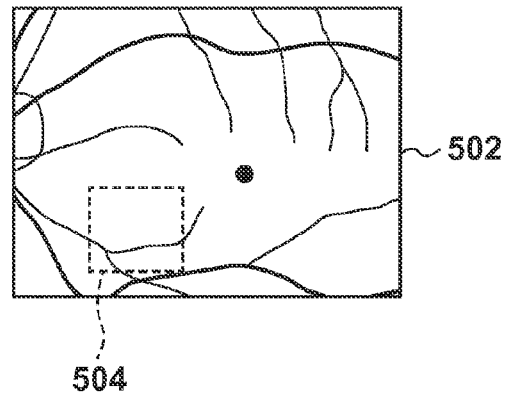

A concrete example will be described with reference to FIGS. 5A and 5B. Fundus images 501 and 502 are fundus images of the same eye 100 captured at different times. An ROI 503 is set on the fundus image 501 and is searched on the image 502. As a result, an ROI 504 having the highest correlation is found. Assume that the position of the ROI 503 and the position of the ROI 504 are respectively represented by (x1, y1) and (x2, y2) in the coordinate system of the fundus image. In this case, a displacement (dx, dy) between the two images is represented by (x2−x1, y2−y1). Note that (x1, y1) may represent arbitrary position coordinates of the ROI 503, and may be, for example, the central coordinates of the ROI 503 or the coordinates of the upper left corner on the drawing surface.

Although this embodiment has exemplified the processing using a contrast or correlation, the embodiment may use any method like an optical flow method as long as it can calculate the relative displacement amount between two images. In addition, the apparatus may not only calculate a translation amount but also set, for example, two or more ROIs on a fundus image and also calculate the rotation amount of the fundus from the calculation results of the movement amounts of the two ROIs.

Figure 3:
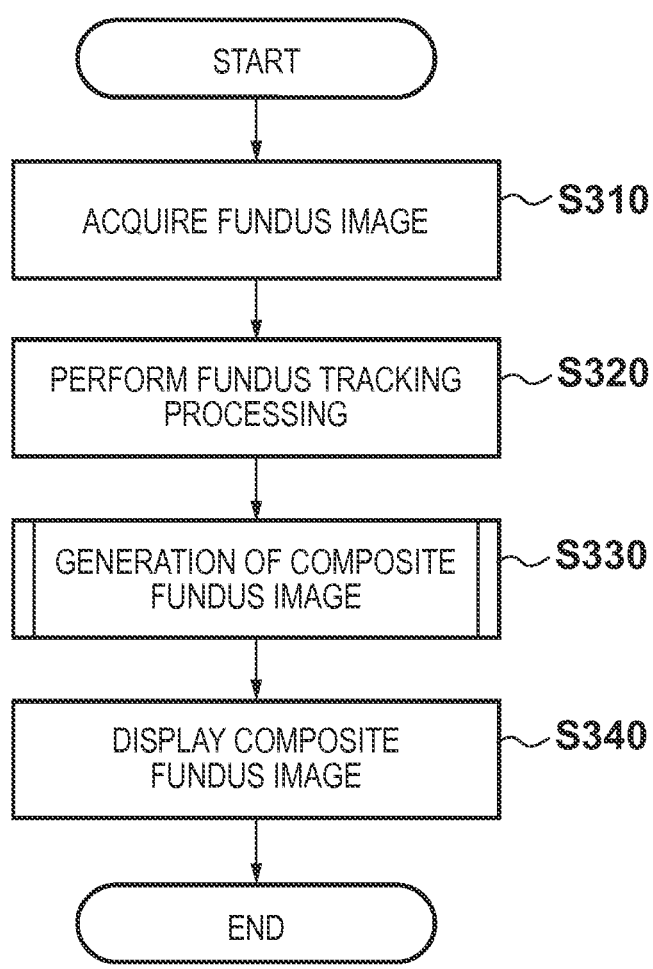
FIG. 3 is a flowchart showing an example of a procedure for processing by the ophthalmic apparatus 10 according to the first embodiment.

A concrete procedure for the processing executed by the ophthalmic apparatus 10 according to the first embodiment will be described next with reference to the flowchart of FIG. 3.

In step S310, the imaging control unit 120A outputs an instruction to capture a fundus image to the imaging unit 110, and acquires the fundus image captured by the imaging unit 110. The imaging control unit 120A outputs the fundus image to the display control unit 120B and the fundus tracking unit 150. In addition, the imaging control information used to capture a tomographic image is output to the display control unit 120B.

In step S320, the fundus tracking unit 150 tracks the fundus and calculates the displacement amount between the fundus images.

In step S330, the display control unit 120B generates a composite fundus image by superimposing the region of interest indicating the imaging position of the tomographic image on the fundus image. In this embodiment, the apparatus generates a composite fundus image upon correcting the superimposing position of a frame indicating the region of interest on the fundus image so as to reduce the displacement based on the displacement amount of the fundus image calculated in step S320. As a result, the apparatus superimposes the region of interest on the same portions (positions) on the sequentially captured fundus images, that is, a specific position on each fundus image. More specifically, assume that the first and second fundus images have been captured at different times. The apparatus superimposes the region of interest on the first fundus image at the position indicated by coordinates (x1, y1) on the first fundus image. Upon calculating a displacement amount (dx, dy) between the first and second fundus images, the apparatus superimposes the region of interest at the position indicated by coordinates (x1+dx, y1+dy) on the second fundus image. That is, the apparatus performs control to move the region of interest on a fundus image and display the region of interest at a predetermined position.

The description about step S330 has exemplified the movement in the lateral direction. When, however, considering the rotation amount of a fundus image as well as a displacement amount, the apparatus may be configured to correct the position of a region of interest by using the rotation amount. In addition, the apparatus may superimpose a region of interest on a fundus image in a tilted state. Furthermore, the apparatus may use other correction methods as long as they can correct the display position of a region of interest based on the displacement amount of the fundus.

In step S340, the display unit 130 displays the composite fundus image generated in step S330. A display example of a composite fundus image on the display unit 130 according to the first embodiment will be described with reference to FIGS. 4A and 4B. FIGS. 4A and 4B show display examples 406 and 407 as image display examples obtained at different times. A fundus image display region 401 is a region for displaying a fundus image. The fundus image display regions 401 respectively display fundus images 408 and 409. A region of interest 402 enclosed by the dotted line indicates the imaging region of a tomographic image. An imaging position 404 of the tomographic image which is indicated by a line segment is one imaging position in the region of interest 402. A tomographic image 405 is a tomographic image captured at the imaging position 404 of the tomographic image. As shown in FIGS. 4A and 4B, as a result of the fine fixation movement of the eye 100, the fundus images 408 and 409 are those captured at different positions on the retina. The apparatus then corrects the superimposing position of the region of interest based on the tracking result (movement displacement amount) between the fundus images 408 and 409, and places the region of interest 402 at the same portion on the fundus. With the above operation, the apparatus terminates each processing of the flowchart of FIG. 3.

As described above, according to this embodiment, when superimposing a region of interest indicating the imaging region, imaging position, and the like of a tomographic image on a fundus image, the apparatus corrects the superimposing position of the region of interest by using the tracking information (displacement amount) between fundus images. That is, the apparatus displays a fundus image and a region of interest indicating the position of a tomographic image so as to locate the region of interest at a predetermined position on the fundus image. This can properly display the region of interest on the fundus image while reducing the influence of fine fixation movement, thereby allowing more accurate comprehension of the imaging position of a tomographic image on a fundus image.

(Second Embodiment)

The first embodiment has exemplified the case in which the apparatus corrects the display position of a region of interest (a region indicating the imaging region and imaging position of a tomographic image) based on the tracking information (displacement amount) between fundus images, moves the region of interest, and superimposes/displays it on the fundus image, thereby allowing accurate comprehension of the imaging position of a tomographic image. In contrast to this, the second embodiment will exemplify a method of controlling the display position of a fundus image based on the tracking information of the fundus image.

The arrangement of an ophthalmic apparatus 10 according to the second embodiment is the same as that described in the first embodiment, and hence a description of it will be omitted. In addition, a procedure for processing according to the second embodiment is the same as that indicated by the flowchart of FIG. 3 in the first embodiment except for step S330, and hence a description of the procedure will be omitted. The following will describe step S330 executed in the second embodiment as step S330B.

In step S330B, a display control unit 120B generates a composite fundus image by superimposing a region of interest indicating the imaging region, imaging position, and the like of a tomographic image on a fundus image. In this embodiment, the apparatus moves pixels of a fundus image based on the displacement amount between fundus images which is calculated in step S320. More specifically, assume that the displacement amount between the first and second fundus images captured at different times is represented by (dx, dy).

Assume that a composite fundus image has the same size as that of the second fundus image, and a composite fundus image (x, y) corresponds to a second fundus image (x+dy, y+dy) with respect to all pixel positions (x, y) of the composite fundus image. In this case, the fundus image (x, y) indicates a pixel value at the pixel position (x, y) at which the fundus image exists. Referring to FIG. 6 to be described later, the apparatus generates a composite image 605 by storing the pixel values of a fundus image 602 and copying pixel values at positions where they cancel displacement amounts.

Figure 6A:
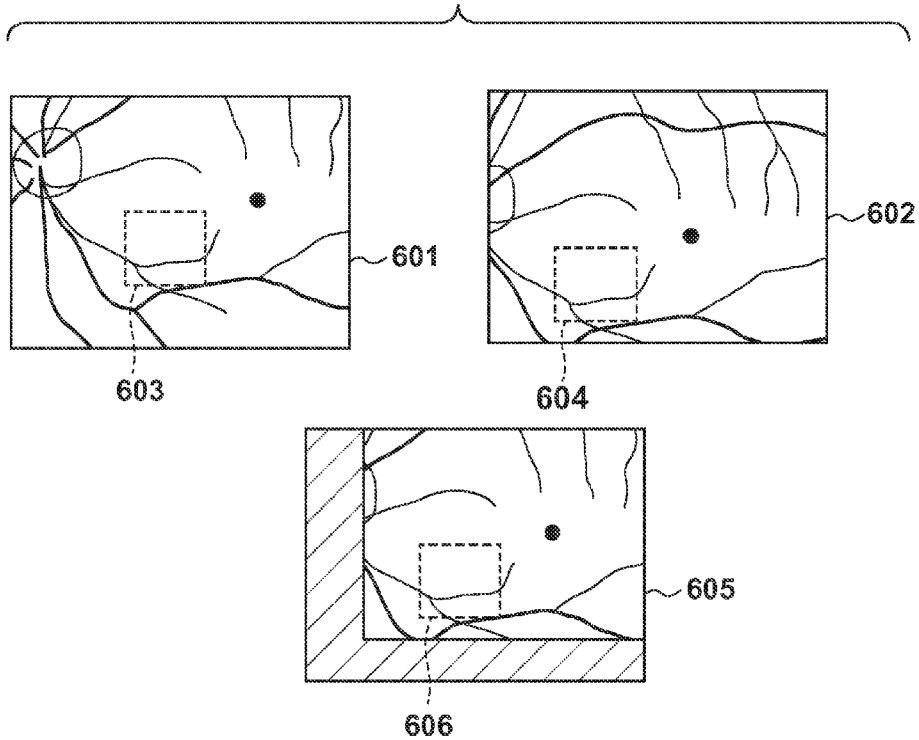
FIGS. 6A and 6B are views each showing a display example of a fundus image on a display unit 130 of an ophthalmic apparatus 10 according to the second embodiment.

A concrete example will be described with reference to FIG. 6A. A fundus image 601 and the fundus image 602 are fundus images of the same eye to be examined which have been captured at different times. Assume that an ROI 604 having the highest correlation with an ROI 603 is found as a result of setting the ROI 603 on the fundus image 601 and searching for a region corresponding to the ROI 603 on the fundus image 602. Assume also that the positions of the ROI 603 and ROI 604 are respectively represented by (xl, yl) and (x2, y2) in the coordinate system of the fundus image. In this case, a displacement amount (dx, dy) between the two images is (x2-xl, y2-yl). As a result of the processing in step S330B, the composite fundus image 605 is generated, and an ROI 606 indicates the same region as the ROI 604. The fundus image of the composite fundus image 605 is the one obtained by moving the fundus image 602 so as to cancel out the displacement amount (dx, dy). The position of the ROI 606 is the same as that of the ROI 603 in the coordinate system of the composite fundus image 605.

Note that in such processing, a region having indeterminate pixel values like the gray region (at the left end and lower end) of the composite fundus image 605 may appear. These pixel values may be expressed by a background color, for example, gray or black, and may be expressed by other colors, oblique lines, and the like. For example, a region having indeterminate pixel values may be made to have pixel values at the same pixel positions as those on the fundus image 601. Alternatively, before the start of the processing in step S330B, a copy of the first fundus image may be used as a composite fundus image. It is possible to eliminate a region having indeterminate pixel values by copying the pixel values of the fundus image 602 on a copy of the first fundus image based on a displacement amount.

According to the above description, in step S330B, the fundus image is moved as a whole. However, a display region of the fundus image may be cut out. The display control unit 120B may cut out part of the fundus image acquired from an imaging unit 110, and may superimpose a region of interest indicating the imaging position and the like of the tomographic image on the cut portion. This can reduce the possibility of the occurrence of a region having indeterminate pixel values.

More specifically, first of all, a display region 1 to be displayed is set on the first fundus image of the first and second fundus images captured at different times. The apparatus then superimposes a region of interest on the image in the display region 1, and outputs the resultant image to the display unit 130. The apparatus then searches for a region having the highest correlation with the display region 1 on the second fundus image, and sets the found region as a display region 2. The apparatus superimposes the region of interest on the display region 2 and outputs the resultant image to a display unit 130.

Figure 6B:
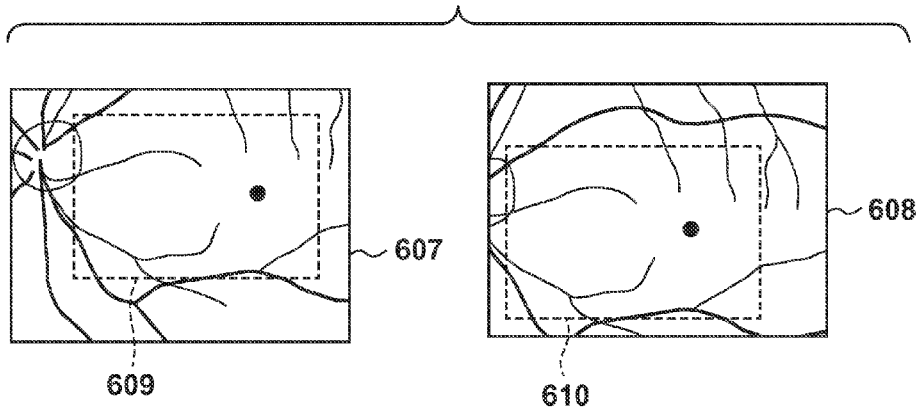

A concrete example will be described with reference to FIG. 6B. Fundus images 607 and 608 are those of the same eye to be examined which have been captured at different times. A display region 609 is set on the fundus image 607. The apparatus then superimposes a region of interest on the display region 609, and displays the resultant image on the display unit 130. The apparatus searches for a display region 610 having the highest correlation with the display region 609 on the fundus image 608. The apparatus superimposes a region of interest on the display region 610, and displays the resultant image on the display unit 130. Since the display unit 130 displays the partial regions 609 and 610 of the fundus image in this manner, it is possible to reduce the possibility of the occurrence of a region having indeterminate pixel values due to the movement of the eye to be examined as compared with the case in which the display unit 130 displays the entire region of the captured fundus image.

As described above, according to this embodiment, when superimposing a region of interest indicating the imaging region, imaging position, and the like of a tomographic image on a fundus image, it is possible to obtain a fundus image with less changes, reduce the movement of the region of interest on the fundus image, and allow easier comprehension of the position of an imaging region on a tomographic image by controlling the display position of the fundus image based on the tracking information of the fundus image.

(Third Embodiment)

The first embodiment has exemplified the case in which the apparatus superimposes and displays a region of interest on a fundus image based on the tracking information of the fundus image to allow accurate comprehension of the imaging position of a tomographic image. In contrast to this, the third embodiment will exemplify a display control method of reducing the movement of a region of interest when the operator operates the region of interest. The arrangement of an ophthalmic apparatus 10 according to the third embodiment is the same as that described in the first embodiment, and hence a description of it will be omitted.

A concrete procedure for the processing executed by the ophthalmic apparatus 10 according to the third embodiment will be described with reference to the flowchart of FIG. 7. Note however that the processing in each of steps S710, S720, and S740 is the same as that in each of steps S310, S320, and S340, and hence a description of it will be omitted.

In step S715, an operation unit 140 outputs an operation signal indicating the operation by the operator to a control unit 120.

In step S730, a display control unit 120B generates a composite fundus image by superimposing a region of interest indicating the imaging position and the like of a tomographic image on the fundus image. More specifically, the display control unit 120B acquires the position of an index which moves on a display unit 130 in accordance with an instruction from the operation unit 140, and determines whether the index is located on the fundus image displayed on the display unit 130. The apparatus uses different fundus image combining methods in accordance with the determination results.

More specifically, the apparatus displays a fundus image in a partial region of the display unit. If an index indicating an arbitrary position on the display unit exists in a region on the display unit other than the partial region, the apparatus moves the region of interest on the display unit based on the calculated displacement. On the other hand, if an index indicating an arbitrary position on the display unit exists on the fundus image, the apparatus stops moving the region of interest.

As described above, if the index does not exist on a fundus image, the apparatus performs the same processing as in step S330. If the index exists on the fundus image, the apparatus superimposes the region of interest at the same position as that of the region of interest on the immediately preceding fundus image without performing correction corresponding to the displacement amount of the fundus image when superimposing the region of interest on the fundus image. That is, the apparatus stops moving the region of interest on the fundus image. The above description has exemplified the case in which the apparatus performs determination depending on whether the index exists on a fundus image. However, the present invention is not limited to this, and the apparatus may perform the determination depending on whether the index exists in the region of interest. More specifically, if the index exists in a region on the display unit other than the region of interest, the apparatus moves the region of interest on the display unit based on a calculated displacement. If the index exists on the region of interest, the apparatus may stop moving the region of interest. Alternatively, if the index exists on the region of interest and the operator performs clicking operation by using a mouse capable of operating the display position of the index, the apparatus may stop moving the region of interest. Note that if the index exists on the fundus image and the operator performs clicking operation, the apparatus may stop moving the region of interest. Stopping the region of interest in this manner will facilitate editing (to be described below) of the region of interest.

In this embodiment, the apparatus may operate a region of interest in accordance with the operation signal input from the operation unit 140. For example, the operator may use a mouse functioning as an instruction unit capable of changing the display position of a region of interest in accordance with the operation of the display position of an index to move the region of interest on the fundus image by clicking the mouse when the index is located on the region of interest and dragging the region of interest while holding the region of interest, or to change the size of the region of interest by dragging an edge of the region of interest while holding it when the index exists on the edge. The apparatus transfers the information of the changed region of interest to an imaging control unit 120A. The imaging control unit 120A calculates a position on the fundus which corresponds to the region of interest, and changes the imaging control information for a tomographic image in an imaging unit 110 so as to capture a tomographic image at a position on the fundus. The imaging control unit 120A then outputs the information to the control unit 120.

More specifically, when the operator clicks the operation unit 140 as a mouse on a fundus image while the index is located on the fundus image, the display control unit 120B receives an operation signal corresponding to the clicking operation. The display control unit 120B then calculates the distance between the coordinate position of the index at the time of the clicking operation and a predetermined position in a region on the display unit 130 on which the fundus image is displayed. The unit of this distance is, for example, a pixel. The apparatus changes the display position of the region of interest in accordance with this calculation result.

Display result examples obtained by the ophthalmic apparatus according to this embodiment will be described with reference to FIGS. 8A to 8D. FIGS. 8A to 8D respectively show display examples 805, 806, 808, and 811 at different times. Fundus image display regions 801 are regions for displaying fundus images. Fundus images 803, 807, 809, and 810 captured at different times are respectively displayed in the fundus image display regions 801 (refer to FIGS. 8A to 8D). Regions of interest 802 respectively show the imaging regions of tomographic images. In the display example 805 in FIG. 8A, since an index 804 is located in the region of interest 802, the superimposing position of the region of interest 802 is the same as that in FIG. 8A, as indicated by the display example 806 in FIG. 8B. When the operator clicks the mouse in the state shown in FIG. 8B, the position of the region of interest 802 is dragged and moved (to the upper left on the drawing surface) by the mouse, as indicated by the display example 808 in FIG. 8C, thereby changing the superimposing position of the region of interest 802 on the fundus image 809. FIG. 8D shows a case in which the size of the region of interest 802 is changed by the operation of the mouse.

As described above, this embodiment facilitates comprehending the imaging position of a tomographic image and operating the imaging position and imaging range of the tomographic image by correcting the superimposing position of a region of interest on a fundus image based on fundus tracking information and the position of the index.

(Fourth Embodiment)

The third embodiment has exemplified the display control method of reducing the movement of a region of interest when the operator operates the region of interest. In contrast to this, the fourth embodiment will exemplify display control on a fundus image when the operator operates a region of interest.

The arrangement of an ophthalmic apparatus 10 according to the fourth embodiment is the same as that described in the first embodiment, and hence a description of it will be omitted. In addition, since a procedure for processing according to the fourth embodiment is the same as the processing procedure indicated by the flowchart of FIG. 7 in the third embodiment except for step S730, a description of the procedure will be omitted. In this case, step S730 executed in the fourth embodiment will be described as step S730B.

In step S730B, a display control unit 120B generates a composite fundus image by superimposing a region of interest indicating the imaging region, imaging position, and the like of a tomographic image on a fundus image. More specifically, the display control unit 120B acquires the position of the index moving on a display unit 130 in accordance with an instruction from an operation unit 140, and determines whether the index exists on the fundus image displayed on the display unit 130. The apparatus uses different fundus image combining methods in accordance with the determination results.

If, for example, the index does not exist on a fundus image, the apparatus performs the same processing as that in step S330. If the index exists on the fundus image, the apparatus performs the same processing as that in step S330B. That is, the apparatus reduces the movement of the region of interest by moving the pixels of the fundus image based on the movement amount between fundus images. Although the above description has exemplified the case in which the apparatus performs determination depending on whether the index exists on the fundus image, the present invention is not limited to this. For example, the apparatus may perform determination depending on whether the index exists in a region of interest. When the operator clicks the mouse capable of operating the display position of the index while the index is located on the region of interest, the apparatus may move the pixels of the fundus image based on the movement amount between the fundus images. Note that when the operator performs clicking operation while the index is located on the fundus image, the apparatus may move the pixels of the fundus image based on the movement amount between the fundus images. Moving the pixels of a fundus image in this manner based on the movement amount between fundus images facilitates editing the region of interest because the region of interest becomes almost still. In this embodiment, as in the third embodiment, the apparatus may operate a region of interest in accordance with an operation signal input from the operation unit 140.

As has been described above, this embodiment facilitates comprehending the imaging position of a tomographic image and also facilitates operating the imaging position and range of the tomographic image by correcting the display method of a fundus image based on fundus tracking information and the position of the index. In addition, since the imaging position of a tomographic image on the fundus is changed little even during the operation of a region of interest, it is possible to more accurately designate an imaging position on the fundus.

Note that the present invention is not limited to the above embodiments, and can be executed while being variously modified and changed within the spirit and scope of the invention. For example, the above embodiments have exemplified fundus tracking. However, the present invention is not limited to this, and may be applied to anterior eye tracking.

According to the present invention, it is possible to properly display a region of interest on a fundus image while reducing the influence of fine fixation movement.

(Other Embodiments)

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-014577 filed on Jan. 26, 2012, which is hereby incorporated by reference herein in its entirety.

What is claimed is:

1. An ophthalmic apparatus comprising:
an acquisition unit which acquires a fundus image of an eye to be examined;
a displacement acquisition unit which acquires a displacement of an imaging position by said acquisition unit between fundus images acquired by said acquisition unit; and
a display control unit which causes a display unit to display the fundus image acquired by said acquisition unit and a region of interest, and which displays the region of interest at a predetermined position on the fundus image, by moving the region of interest on the display unit based on the displacement acquired by said displacement acquisition unit,
wherein said display control unit moves the region of interest on the display unit based on the displacement acquired by said displacement acquisition unit in a case where an indication indicating an arbitrary position of the display unit is located on a region on the display unit other than the region of interest, and stops the movement of the region of interest in a case where the indication is located on the region of interest.

2. The apparatus according to claim 1, wherein said display control unit moves the region of interest on the display unit based on the displacement acquired by said displacement acquisition unit in a case where the indication is located on a region on the display unit other than the region of interest, and stops the movement of the region of interest, in a case where the indication is located on the region of interest and a predetermined operation is performed by an examiner on an operation unit.

3. The apparatus according to claim 2, wherein the operation unit is a mouse and the predetermined operation is a click.

4. The apparatus according to claim 3, wherein the predetermined position is changeable.

5. The apparatus according to claim 3, wherein the predetermined position is determined by a designation of an operator.

6. The apparatus according to claim 3, wherein the region of interest is a region in which a tomogram of the fundus is captured.

7. The apparatus according to claim 1, wherein the predetermined position is changeable.

8. The apparatus according to claim 1, wherein the predetermined position is determined by a designation of an operator.

9. The apparatus according to claim 1, wherein the region of interest is a region in which a tomogram of the fundus is captured.

10. An ophthalmic apparatus comprising:
an acquisition unit which acquires a fundus image of an eye to be examined;
a displacement acquisition unit which acquires a displacement of an imaging position by said acquisition unit between fundus images acquired by said acquisition unit; and
a display control unit which causes a display unit to display the fundus image acquired by said acquisition unit and a region of interest, and which displays the region of interest at a predetermined position on the fundus image, by moving the region of interest on the display unit based on the displacement acquired by said displacement acquisition unit,
wherein said display control unit displays the fundus image on a part of a region of the display unit, and moves the region of interest on the display unit based on the displacement acquired by said displacement acquisition unit in a case where an indication indicating an arbitrary position of the display unit is located on a region on the display unit other than the part of the region, and stops the movement of the region of interest in a case where the indication is located on the fundus image.

11. The apparatus according to claim 10, wherein said display control unit moves the region of interest on the display unit based on the displacement acquired by said displacement acquisition unit in a case where the indication is located on a region on the display unit other than the part of the region, and stops the movement of the region of interest, in a case where the indication is located on the part of the region and a predetermined operation is performed by an examiner on an operation unit.

12. The apparatus according to claim 11, wherein the operation unit is a mouse and the predetermined operation is a click.

13. A control method for an ophthalmic apparatus comprising an acquisition unit, a displacement acquisition unit, and a display control unit, the method comprising:
an acquisition step of causing the acquisition unit to acquire a fundus image of an eye to be examined;
a displacement acquisition step of causing the displacement acquisition unit to acquire a displacement of an imaging position by the acquisition unit between fundus images acquired in the acquisition step; and
a display control step of causing the display control unit to cause a display unit to display the fundus image acquired in the acquisition step and a region of interest, with the region of interest being displayed at a predetermined position on the fundus image, by moving the region of interest on the display unit based on the displacement acquired in the displacement acquisition step,
wherein in the display control step, the display control unit moves the region of interest on the display unit based on the displacement acquired in the displacement acquisition step in a case where an indication indicating an arbitrary position of the display unit is located on a region on the display unit other than the region of interest, and stops the movement of the region of interest in a case where the indication is located on the region of interest.

14. The control method according to claim 13, wherein the predetermined position is changeable.

15. The control method according to claim 13, wherein the predetermined position is determined by a designation of an operator.

16. The control method according to claim 13, wherein the region of interest is a region in which a tomogram of the fundus is captured.

17. A control method for an ophthalmic apparatus comprising an acquisition unit, a displacement acquisition unit, and a display control unit, the method comprising:
an acquisition step of causing the acquisition unit to acquire a fundus image of an eye to be examined;
a displacement acquisition step of causing the displacement acquisition unit to acquire a displacement of an imaging position by the acquisition unit between fundus images acquired in the acquisition step; and
a display control step of causing the display control unit to cause a display unit to display the fundus image acquired in the acquisition step and a region of interest, wherein the region of interest is displayed at a predetermined position on the fundus image, by moving the region of interest on the display unit based on the displacement acquired in the displacement acquisition step,
wherein in the display control step, the display control unit displays the fundus image on a part of a region of the display unit, and moves the region of interest on the display unit based on the displacement acquired in said displacement acquisition step in a case where an indication indicating an arbitrary position of the display unit is located on a region on the display unit other than the part of the region, and stops the movement of the region of interest in a case where the indication is located on the fundus image.

18. The control method according to claim 17, wherein the predetermined position is changeable.

19. The control method according to claim 17, wherein the predetermined position is determined by a designation of an operator.

20. The control method according to claim 17, wherein the region of interest is a region in which a tomogram of the fundus is captured.

* * * * *